United States Patent [19]

Makovec et al.

[11] Patent Number: 5,130,474
[45] Date of Patent: Jul. 14, 1992

[54] OPTICALLY-ACTIVE DERIVATIVES OF (R) 5-PENTYLAMINO-5-OXOPENTANOIC ACID WITH ANTAGONISTIC ACTIVITY TOWARDS CHOLECYSTOKININ AND A METHOD FOR THEIR PREPARATION

[75] Inventors: Francesco Makovec; Rolando Chiste, both of Monza; Walter Peris, Milano; Luigi Rovati, Monza, all of Italy

[73] Assignee: Rotta Research Laboratorium SpA, Milano, Italy

[21] Appl. No.: 637,583

[22] Filed: Jan. 4, 1991

Related U.S. Application Data

[60] Division of Ser. No. 425,148, Oct. 23, 1989, which is a continuation of Ser. No. 152,724, Feb. 5, 1988, abandoned.

[30] Foreign Application Priority Data

Feb. 5, 1987 [IT] Italy ............... 67076 A/87

[51] Int. Cl.$^5$ ........................... C07C 279/00
[52] U.S. Cl. ........................ 562/448; 562/450; 562/449
[58] Field of Search ................ 562/448, 450

[56] References Cited

U.S. PATENT DOCUMENTS 3,551,417  12/1970  Da Re et al. ............... 562/450
4,250,183   2/1981  Krastinat .................. 562/448
4,769,389   7/1988  Makovec et al. ........... 562/450

FOREIGN PATENT DOCUMENTS 2049332  10/1970  Fed. Rep. of Germany ...... 562/450
8703869   7/1987  Italy ...................... 562/448
0272228   6/1988  Italy ...................... 562/450

Primary Examiner—Jose G. Dees
Assistant Examiner—Keith D. MacMillan
Attorney, Agent, or Firm—Sughrue, Mion, Zinn Macpeak & Seas

[57] ABSTRACT

There are described optically active derivatives (R) 5-pentylamino-5-oxopentanoic acid and their pharmaceutically acceptable salts, having antagonistic activity towards cholecystokinin, and with the formula:

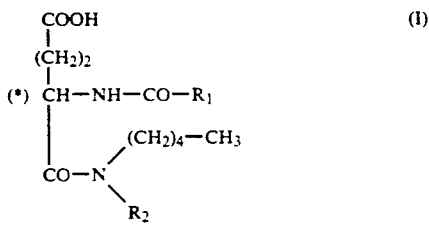

in which $R_1$ is selected from the groups 2-naphthyl, 3,4-dichlorobenzoyl and 3,4-dimethylbenzoyl and $R_2$ is a pentyl group or an alkoxyalkyl group with 4 carbon atoms, and in which the substituents on the central chiral group (marked with an asterisk in Formula (I)), have the R (rectus) conformation.

3 Claims, No Drawings

OPTICALLY-ACTIVE DERIVATIVES OF (R) 5-PENTYLAMINO-5-OXOPENTANOIC ACID WITH ANTAGONISTIC ACTIVITY TOWARDS CHOLECYSTOKININ AND A METHOD FOR THEIR PREPARATION

This is a divisional of application Ser. No. 07/425,148 filed Oct. 23, 1989 which is a continuation of application Ser. No. 07/152,724 filed Feb. 5, 1988, abandoned.

DESCRIPTION

The subjects of the present invention are original derivatives of (R) 5-pentylamino-5-oxopentanoic acid, which may be represented by the general formula indicated below:

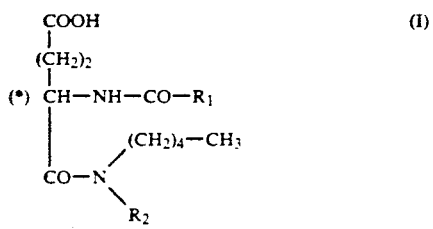

in which $R_1$ is selected from the groups 2-naphthyl, 3,4-dichlorobenzoyl and 3,4-dimethyl-benzoyl and $R_2$ is a pentyl group or an alkoxyalkyl group with 4 carbon atoms, and in which the substituents on the central chiral group (marked with an aserisk in Formula (I)) have the R (rectus) conformation.

$R_2$ is preferably selected from the group consisting of the pentyl, 2-ethoxyethyl and 3-methoxypropyl groups.

The compounds which are the subject of the present invention display a powerful antagonistic activity towards cholecystokinin (CCK). The compounds according to the invention may thus be used to advantage in the treatment of various illnesses in man, such as illnesses of the digestive system, as for example, in the treatment of colitis, of biliary diskinesia and pancreatitis.

On the basis of their pharmacological characteristics, their use may also be envisaged in the treatment of mental disorders attributable to deficiencies in the physiological neuron levels of CCK or of other related bioactive polypeptides and also in the treatment of anorexia.

The compounds which are the subject of this invention, as already mentioned, have a powerful anti-CCK activity in various experimental situations, both in vivo and in vitro.

Thus, in nanomolar concentrations, they inhibit the binding of marked cholecystokinin to the cell membranes of the gallbladder of an ox, a tissue which is considered to be a target organ for the physiological action of cholecystokinin.

Moreover, these compounds are also very active in vivo. For example, they inhibit, in a dose-dependent manner, some even with a dose of less than 0.1 mg/kg, the contraction and emptying of the gallbladder induced by egg yolk, which is an inducer for the endogenous release of CCK. They also encourage emptying of the stomach by inhibiting the piloric contraction caused by CCK.

Moreover their protective action is particularly powerful against experimental pancreatitis, for example, against pancreatitis induced by sodium taurocholate.

Pharmaceutical forms of the compounds which are the subject of the invention may be prepared by conventional techniques, for example as pills, capsules, suspensions, solutions and suppositories and may be administered orally, parenterally or rectally.

The active ingredient is administered to the patient typically in a ratio of 0.005 to 5 mg/kg of body weight per dose. For parenteral administration, it is preferable to use a water-soluble salt of the subject compounds, such as the sodium salt or another salt which is non-toxic and pharmaceutically acceptable. Substances commonly used in the pharmaceutical industry as excipients, binders, flavourings, dispersants, colouring agents, humectants, etc. may be used as inactive ingredients.

These derivatives of 5-pentylamino-5-oxopentanoic acid form part of a class of compounds which is the subject of earlier Patents of the Applicant which describe a method for producing the subject compounds, but in the racemic form (R,S) starting from L-glutamic acid.

The present invention arises from the following two considerations:

A) the anti-cholecystokinin activity of the compounds which are the subject of the patents mentioned above is due to the enantiomeric R forms, which correspond to the starting D-glutamic acid. This fact is quite surprising considering the fact that the natural aminoacids which are biologically active all belong to the L series.

B) The method described previously does not enable configuration to be retained; that is, whether L-glutamic acid or D-glutamic acid was used as the starting material, (R,S) derivatives of pentanoic acid were produced.

Another object of the present invention is, therefore, to provide a method which ensures that configuration is retained in successive transformations and which therefore enables the 5-pentylamino-5-oxopentanoic derivatives to be obtained from D-glutamic acid in the optically active R (rectus) form which is the pharmacoloigcally-active enantiomeric form.

The method for the preparation of the derivatives which are the subject of the present invention, is characterised in that is comprises the steps of:

a) reacting the gamma-benzyl ester of N-carbobenzoxy-D-glutamic acid with an amine of formula

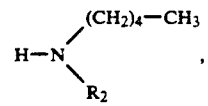

in which $R_2$ has the meaning attributed to it above, by the mixed anhydride method in an inert anhydrous solvent at a temperature of between $-15°$ and $+15°$ to give the compounds of formula (III); (see reaction scheme below)

b) debenzylating and decarbobenzoxylating the compound of formula (III) dissolved in an inert solvent by reacting it with hydrogen at ambient temperature and atmospheric pressure in the presence of a catalytically effective quantity of a hydrogenation catalyst to obtain the derivatives of formula (II) (see scheme below)

c) reacting the derivatives of formula (II) under Schotten-Bauman conditions with an equivalent quantity of an acyl chloride of formula $R_1$—COCl, in which $R_1$ has the meaning attributed to it above, at a temperature of from 0° to 15° C. and recovering the (R) 4-acylamino-5-pentylamino-5-oxopentanoic derivatives of formula (I) from the reaction mass.

The series of steps of the method according to the invention is illustrated as a whole in the following reaction scheme:

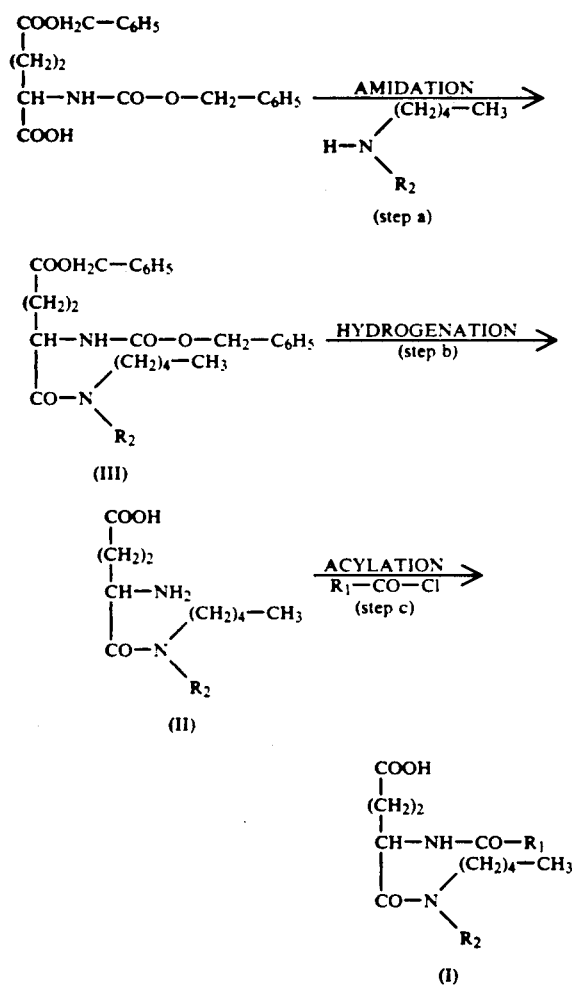

The amidation step (a) is carried out preferably at a temperature of between −15° and −10° C. over a period of from 1 to 24 hours, preferably for 6 hours with the reagents in a stoichiometric ratio. The preferred solvent for the reaction is selected from chloroform, dioxan and tetrahydrofuran.

The hydrogenation step (b) is preferably carried out in the presence of palladium supported on carbon, with between 0.02 and 0.001 atoms of palladium per mole of compound (III), in a methanolic solution, at ambient temperature and pressure, in a stream of hydrogen for a period of from 1 to 12 hours, preferably 3 hours. The acylation step (c) is preferably carried out at a temperature of approximately 5° C. for a period of from 1 to 24 hours, preferably 12 hours.

The following examples are given in order better to illustrate the invention.

EXAMPLE 1

Preparation of the benzyl ester of (R) 4-carbobenzoxyamino-5-(di-n-pentylamino)-5-oxopentanoic acid (compound 1 of Table 1). 37.1 g (0.1 moles) of the gamma-benzyl ester of N-carbobenzoxy-D-glutamic acid are dissolved in 250 ml of anhydrous tetrahydrofuran, the solution is cooled to −10° C. and 10.1 g (0.1 moles) of triethylamine are added with agitation; 10.8 g (0.1 moles) of ethyl chlorocarbonate are then added, still at −10° C. The temperature is maintained at −10° C. for 20 minutes and then 15.7 g (0.1 moles) of di-pentylamine are added. Agitation is continued for a further 6 hours and the temperature rises to ambient temperature; it is dried and the residue is taken up in ethyl acetate.

It is washed with 2N HCl, sodium bicarbonate and finally with water; then it is dried over anhydrous $Na_2SO_4$. By concentration to small volume, an oily residue is obtained (mw 510.6), which does not crystallise, with a chromatographic purity of more than 95%.

TLC: Rf 0.81 (chloroform-ethyl acetate 7/3 V/V). 46.5 g obtained. Yield 91%.

All the compounds of formula III are crystallised by the same method (see scheme above). The compounds obtained are shown with some identifying characteristics as well as the yields obtained in Table 1 below.

EXAMPLE 2

Preparation of (R) 4-amino-5-(di-n-pentylamino)-5-oxopentanoic acid (compound 4 of table 2)

51.1 g (0.1 moles) of the benzyl ester of (R) 4-carbobenzoxyamino-5-(di-n-pentylamino)-5-oxopentanoic acid are dissolved in 300 ml of methanol, with the addition of 1 g of carbon palladiate at 10% and hydrogenated at ambient temperature with a stream of hydrogen for 3 hours. The catalyst is filtered off and the methanol is distilled under vacuum. An oily residue is obtained (mw 286.4) which does not crystallise, with a chromatographic purity of more than 95%.

TLC: Rf 0.75 (n-Butanol-acetic acid-$H_2O$ 5/2/2 V/V/V).

All the compounds of formula II are synthesised by the same method (see scheme).

The compounds obtained are shown with some identifying characteristics as well as the yields obtained below.

EXAMPLE 3

Preparation of (R) 4-(2-naphthylamino)-5-(di-n-pentylamino)-5-oxopentanoic acid, (Compound 7 of Table 3)

28.6 g (0.1 moles) of (R) 4-amino-5-(di-n-pentylamino)-5-oxopentanoic acid are suspended in 300 ml of water and then dissolved with agitation by the addition of 10.6 g (0.1 moles) of sodium carbonate. Then 19.1 g (0.1 moles) of 2-naphthoyl chloride are added in 1 hour at 0° C. with agitation.

The mixture is left for 12 hours to react.

It is made acid to Congo red with dilute HCl and the precipitate thus formed is filtered off. It is crystallised from $H_2O$-ethanol (2/1).

M.P.69°-72° C. TLC (iso-amyl alcohol-acetone-$H_2O$: 5/2/1): Rf 0.83 37 g obtained (mw 440.6) Yield 84%.

Rotary power: [alpha] $D^{20} = +11.0$ (c=2.5% in 95% ethanol).

All compounds of formula I (see scheme) are synthesized by the same method.

Some examples of these compounds with some identifying characteristics as well as the yields obtained are given by way of example in Table 3 below.

In order to compare the anti-CCK activity of the derivatives of (R) 5-pentylamino-5-oxopentanoic acid with the corresponding (S) series enantiomers, some of these derivatives were synthesised by the method described above but, in this case, starting from the gamma-benzylester of N-carbobenzoxy-L-glutamic acid.

Table 4 shows some of the (S) 4-acylamino-5-(di-n-pentylamino)-5-oxopentanoic derivatives thus obtained and used for the pharmacological comparisons with some of their identifying characteristics.

TABLE 1 derivatives having the formula:

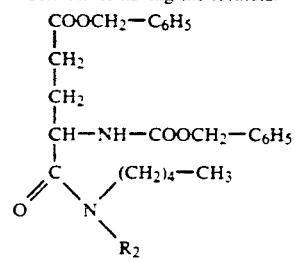

| Compound | $R_2$ | Rf(*) | Formula |
|---|---|---|---|
| 1 | pentyl | 0.71 | $C_{30}H_{42}N_2O_5$ |
| 2 | 3-methoxypropyl | 0.22 | $C_{29}H_{40}N_2O_6$ |

TABLE 1-continued derivatives having the formula:

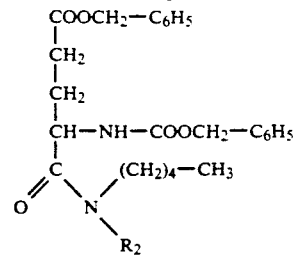

| Compound | $R_2$ | Rf(*) | Formula |
|---|---|---|---|
| 3 | 2-ethoxyethyl | 0.28 | $C_{29}H_{40}N_2O_6$ |

(*) eluents: chloroform/ethyl acetate 9/1-V/V

TABLE 2 derivatives having the formula

COOH
|
$CH_2$
|
$CH_2$
|
$CH-NH_2$
|
C—N—$(CH_2)_4$—$CH_3$
with =O and $R_2$

| Compound | $R_2$ | Rf(*) | Formula |
|---|---|---|---|
| 4 | pentyl | 0.73 | $C_{15}H_{30}N_2O_3$ |
| 5 | 3-methoxypropyl | 0.58 | $C_{14}H_{28}N_2O_4$ |
| 6 | 2-ethoxyethyl | 0.62 | $C_{14}H_{28}N_2O_4$ |

(*) eluents: n-Butanol-Acetic acid - $H_2O$: 5/2/2-V/V

TABLE 3

(R Series) derivatives having the formula

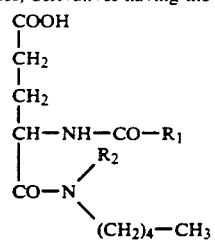

| Compound | $R_1$ | $R_2$ | Melting point (°C.) | Solvents of crystallisation | Rf (*) | Yield (**) | Rotatory Power | Formula |
|---|---|---|---|---|---|---|---|---|
| 7 | 2-naphthyl | pentyl | 83–86 | water/alcohol (2:1) | 0.84 | 68.8 | +11.0 | $C_{26}H_{36}N_2O_4$ |
| 8 | 3,4-dichlorophenyl | pentyl | 111–4 | isopropyl ether | 0.87 | 63.8 | +17.0 | $C_{22}H_{32}Cl_2N_2O_4$ |
| 9 | 3,4-dimethylphenyl | pentyl | 79–31 | isopropyl ether | 0.82 | 50.7 | +15.6 | $C_{24}H_{38}N_2O_4$ |
| 10 | 2-naphthyl | 3-methoxypropyl | 57–60 | water/alcohol (2:1) | 0.66 | 52.6 | +6.2 | $C_{25}H_{34}N_2O_5$ |
| 11 | 3,4-dichlorophenyl | 3-methoxypropyl | 97–100 | water/alcohol (2:1) | 0.78 | 47.7 | +9.5 | $C_{21}H_{30}Cl_2N_2O_5$ |
| 12 | 2-naphthyl | 2-ethoxyethyl | 68–72 | water/alcohol (2:1) | 0.68 | 48.5 | +6.0 | $C_{25}H_{34}N_2O_5$ |

(*) eluents: iso-amyl alcohol/acetone/water: 5/2/1-V/V (**) Calculated yield starting from the gamma-benzyl ester of N-carbobenzoxy-D-glutamic acid

TABLE 4

(S Series) derivatives having the formula

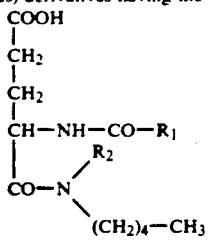

| Compound | $R_1$ | $R_2$ | Melting point (°C.) | Solvents of crystallisation | Rf(*) | Rotatory Power [alpha] $D^{20}$ | Formula |
| --- | --- | --- | --- | --- | --- | --- | --- |
| 13 | 2-naphthyl | pentyl | 70–73 | water/alcohol (2:1) | 0.84 | −11.0 | $C_{26}H_{36}N_2O_4$ |
| 14 | 3,4-dichlorophenyl | pentyl | 88–90 | isopropyl ether | 0.86 | −16.6 | $C_{22}H_{32}Cl_2N_2O_4$ |
| 15 | 3,4-dimethylphenyl | pentyl | 75-7 | isopropyl ether | 0.81 | −15.2 | $C_{24}H_{38}N_2O_4$ |
| 16 | 2-naphthyl | 3-methoxypropyl | 51-3 | water/alcohol (2:1) | 0.65 | −6.0 | $C_{25}H_{34}N_2O_5$ |

(*) eluents: iso-amyl alcohol/acetone/water: 5/2/1-V/V

The powerful anti-cholecystokinin activity of the compounds which are the subject of the invention will now be documented by a series of pharmacological experiments conducted both in vitro and in vivo.

Studies on binding to cell membranes of ox gallbladders

The capacity of some of the compounds of the invention and of some of the corresponding (S series) enantiomers to inhibit the binding of [125-I]-Bolton Hunter-CCK-8 to the cholecystokinin receptors of ox gallbladder membranes was evaluated by comparison with the displacement induced by cold (unmarked) CCK.

The ox gallbladder cell membranes were homogenised with Tris buffer (pH 7.4) and the homogenate was centrifuged at 50,000 gravity for 10 minutes. The membranes were then incubated with a radioactive tracer and the compounds under study for 2 h at 25° C.

After the supernatant liquid had been discarded, the radioactivity associated with the pellet was determined with a liquid scintillator. The specific binding was determined as the difference between the binding in the absence and in the presence of $10^{-6}M$ CCK-8.

The results thus obtained are given in Table 5, in which the IC50 is shown, that is the concentration (in moles/litre) of the antagonist able to displace 50% of the [125-I]-CCK-8 from the receptors.

TABLE 5

Inhibition of the binding of $(^{125}I)$-(B-H)-CCK-8

| Compounds (R Series) | IC50 (moles/liter) | Compounds (S Series) | IC50 (moles/liter) |
| --- | --- | --- | --- |
| CCK-8 | $0.2 \times 10^{-9}$ | Compound 13 | $6.1 \times 10^{-8}$ |
| Compound 7 | $1.0 \times 10^{-9}$ | Compound 14 | $4.5 \times 10^{-7}$ |
| Compound 8 | $7.5 \times 10^{-9}$ | Compound 15 | $2.2 \times 10^{-6}$ |
| Compound 9 | $4.4 \times 10^{-8}$ | Compound 16 | $5.6 \times 10^{-7}$ |
| Compound 10 | $6.2 \times 10^{-9}$ | | |
| Compound 11 | $3.0 \times 10^{-8}$ | | |
| Compound 12 | $9.3 \times 10^{-9}$ | | |

From the data given in the table it can be seen that the claimed compounds antagonise 50% of the binding of CCK at a concentration which, for the most active compound of the R series, is only 5 times greater than that of the specific antagonist, thus showing a very high specificity of action. The corresponding S-series enantiomers are on average 50–90 times less active.

In order to confirm what was shown by this in vitro study, some of the compounds were also tested in vivo.

Antispastic activity on the gallbladder in mice

The emptying of the gallbladder was induced by a single oral administration of 1 ml of a 30% suspension (weight/volume) of lyophilised egg yolk in a physiological solution.

Once it has been absorbed, the egg yolk, as stated above, induces the release of endogenous CCK. This dose was selected as it causes practically complete emptying of the gallbladder.

The antagonist compounds were administered intraperitoneally (i.p.) 15 minutes before the contractant.

The % antispastic activity for each dose was calculated by the following formula:

$$\% = \frac{P_1 - P_2}{P_3 - P_2} \times 100$$

where $P_1$ = average weight of the gallbladders of the group of animals treated with the drug plus the contractant $P_2$ = average weight of the gallbladders of the group of animals treated with contractant only $P_3$ = average weight of the gallbladders of the control group of animals.

The compounds were tested in various doses so as to enable the calculation of the ID50 value, that is the dose (in mg/kg i.p.) which is able to inhibit the contractant effect of the egg yolk by 50%.

The results thus obtained are given in Table 6, where the effects obtained are expressed as the ID50.

TABLE 6

| | Antispastic activity on gallbladder contraction induced by egg yolk. | | |
| --- | --- | --- | --- |
| Compound | Doses (mg/kg i.p.) | % inhibition of the emptying of the gallbladder | ID50 (1) (mg/kg i.p.) |
| 7 (R Series) | 0.025 | 24.0 | 0.05 |
| | 0.05 | 44.2 | |
| | 0.1 | 74.0 | (0.99) |
| 8 (R-Series) | 0.1 | 25.2 | 0.25 |
| | 0.3 | 53.2 | |
| | 0.1 | 86.3 | (0.99) |
| 13 (S-Series) | 1 | 18.8 | 3.2 |
| | 3 | 47.7 | |
| | 9 | 80.2 | (0.99) |
| ATROPINE | 5 | 3.7 | |
| | 10 | 21.6 | INACTIVE |
| | 15 | 10.5 | |

TABLE 6-continued

| | Antispastic activity on gallbladder contraction induced by egg yolk | | |
|---|---|---|---|
| Compound | Doses (mg/kg i.p.) | % inhibition of the emptying of the gallbladder | ID50 (1) (mg/kg i.p.) |
| PAPAVERINE | 25 | 0 | |
| | 50 | 0 | INACTIVE |
| | 75 | 26.1 | |

(1) r = the coefficient of correlation of the straight line of regression. The emptying of the gallbladder is reduced in a dose-dependent manner by the compounds which are the subject of the invention. Compound 7, at a dose of 0.1 mg/kg, blocks the contraction induced by the egg yolk by approximately 75%. Its (S) enantiomer is also active but with an ID50 value approximately 60 times larger. Atropine, on the other hand is inactive and papeverine is slightly active, but only at the toxic dose of 75 mg/kg, which causes the death of 20% of the animals treated.

Antispastic activity on piloric contraction in rats

This experiment shows the contractant effect of CCK on the piloric sphincter. A dose of 8 mcg/kg i.p. of CCK was used, which induces a sub-maximal contraction of the pilorus.

The antagonistic compounds were administered (i.p.) 15 minutes before the contractant. 10 minutes after the administration of the contractant, the animals were treated per os with 25 ml/kg of $H_2O$. 5 minutes after this administration, the animals were killed, their stomachs removed and the gastric content measured by removal with a syringe.

The % antispactic activity for each dose administered was calculated from the following formula:

$$\%_c = \frac{V_2 - V_1}{V_2 - V_3} \times 100$$

where $V_1$ = the gastric-content volume of the group of animals treated with the drug plus the contractant $V_2$ = the gastric-content volume of the group of animals treated with the contractant only $V_3$ = the gastric-content volume of the control group of animals.

The compounds were tested at various doses so as to enable the calculation of the ID50 value, that is the dose (in mg/kg i.p.) which is able to inhibit the contractant effect of CCK by 50%.

The results obtained are given in Table 7, where the effects obtained are expressed as the ID50.

TABLE 7

| | Antispastic activity on piloric contraction induced by CCK in the rat. | | |
|---|---|---|---|
| Compound | Doses (mg/kg i.p.) | % inhibition of piloric contraction | ID50 (1) (mg/kg i.p.) |
| 7 (R Series) | 0.01 | 27.7 | |
| | 0.03 | 48.8 | 0.03 |
| | 0.1 | 80.8 | (0.99) |
| 8 (R-Series) | 0.03 | 29.8 | |
| | 0.1 | 48.0 | 0.11 |
| | 0.3 | 68.1 | (0.99) |
| 13 (S-Series) | 1 | 17.7 | 4.55 |
| | 3 | 39.0 | |
| | 5 | 54.2 | (0.99) |

(1): in brackets r = the coefficient of correlation of the straight line of regression.

The piloric contraction caused by 8 mcg/kg of CCK-8 is inhibited by 50% by some of the compounds of the invention at very low doses, 30 mcg/kg in the case of compound 7, that is at dose only 3-4 times greater than that of the hormonal contractant. Compound 13, on the other hand, which is the S enantiomer of compound 7, is active only at doses approximately 150 times higher.

Pancreatitis induced by sodium taurocholate

The method described by Aho et al. (Scandinavian J. Gastroenterology 15 (1980), 411-16) was followed Male rats weighing approximately 250 g were subjected to laparatomy and the pancreas exposed. 0.3 ml of a 6% solution of sodium taurocholate was injected directly into the pancreatic tissue.

The products under test were administered intraperitoneally (i.p.) 30 minutes before the operation and 3 hours after the operation. 6 hours after the laparotomy and after anesthesia with ether, blood was removed from the retro-orbital plexus, the animals were killed and the pancreas removed and weighed. The activity of the serum amylase was determined by the Ceska method (Clin. Chim. Acta 26 (1969), 437-444).

The compounds were tested at different doses so as to enable the calculation of the ID50 value, that is the dose (in mg/kg i.p.) which is able to inhibit the toxic effect of the sodium taurocholate by 50%, expressed both as a % inhibition of the increase in weight of the pancreas and as a % inhibition of the increase in serum amylase. The results obtained with compounds 7 and 8 are given in Table 8.

TABLE 8

| | Examples of proteolytic activity of the claimed compounds in experimental - pancreatitis induced by taurocholate in rats | | | |
|---|---|---|---|---|
| | % ratio pancreas weight animal weight | % Inhibition of weight increase (ID50 mg/kg ip) | Amylase in the serum (U/ml) | % Inhibition increase in amylase (ID50 mg/kg ip) |
| Controls | 0.40 | — | 8.3 | — |
| Controls + Taurocholate | 0.51 | — | 14.7 | — |
| Compound 7 (0.3 mg/kg) + Taurocholate | 0.47 | 36.4 | 12.0 | 42.2 |
| Compound 7 (1 mg/kg) + Taurocholate | 0.45 | 54.5 | 9.6 | 79.7 |
| Compound 7 (3 mg/kg) + Taurocholate | 0.41 | 90.8 | 9.0 | 89.0 |

TABLE 8-continued

Examples of proteolytic activity of the claimed compounds in experimental - pancreatitis induced by taurocholate in rats

| | % ratio pancreas weight animal weight | % Inhibition of weight increase (ID50 mg/kg ip) | Amylase in the serum (U/ml) | % Inhibition increase in amylase (ID50 mg/kg ip) |
|---|---|---|---|---|
| | ID50 = 0.6 | (r = 0.98) | ID50 = 0.4 | (r = 0.94) |
| Controls | 0.37 | — | 7.9 | — |
| Controls + Taurocholate | 0.54 | — | 16.0 | — |
| Compound 8 (1.0 mg/kg) + Taurocholate | 0.48 | 35.3 | 12.7 | 40.7 |
| Compound 8 (5 mg/kg) + Taurocholate | 0.45 | 52.5 | 9.8 | 76.5 |
| Compound 8 (5 mg/kg) + Taurocholate | 0.40 | 82.3 | 9.0 | 86.4 |
| | ID50 = 1.8 | (r = 0.97) | ID50 = 1.2 | (r = 0.97) |

(r) = correlation coefficient

Sodium taurocholate induces pancreatitis which causes an increase in weight of the organ which also becomes oedematous, lacking in elasticity and haemorrhagic.

Moreover, the serum amylase almost doubles. These effects are blocked in a dose-dependent manner by the compounds which are the subject of the invention. For example, a dose of approximately 0.5 mg/kg i.p. of the compound 7 inhibits the increase in weight of the pancreas and the increase in serum amylase by 50%.

The experimental data given above have thus shown the possible utility of these compounds in the treatment of various pathalogical conditions affecting the gastrointestinal tract, for example in spastic syndromes and pain generally, such as biliary diskinesia, or for encouraging emptying of the stomach and thus encouraging digestion.

These products could be used to particular advantage for the treatment of pancreatitis since safely active drugs whose efficacy has been shown by pertinent pharmacological experiments are lacking for this pathological condition. A favourable therapeutic use can also be envisaged for many of the subject compounds in the treatment of various forms of anorexia and also in the treatment of some pathological conditions of the CNS linked to deficiencies in the physiological neuron levels of CCK or other bioactive peptides.

We claim:

1. A method for the preparation of a derivative of (R) 5-pentylamino-5-oxopentanoic acid having the formula (I):

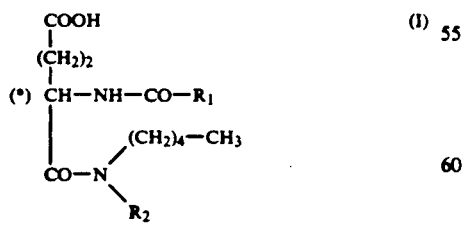

in which $R_1$ is selected from the groups 2-naphthyl, 3,4-dichlorobenzoyl and 3,4-dimethylbenzoyl, and $R_2$ is selected from the pentyl group and alkoxyalkyl groups with 4 carbon atoms in which the substituents on the central chiral group (marked with an asterisk in formula (I)) have the R (rectus) conformation, including the steps of:

a) reacting, by the mixed anhydride method, the gamma-benzyl ester or N-carbobenzoxy-D-glutamic acid with an amine having the formula

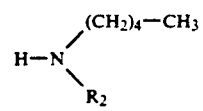

in which $R_2$ has the meaning attributed to it above, at a temperature of from $-15°$ C. to $+15°$ C. in an inert anhydrous solvent and recovering from the reaction mass the compound III,

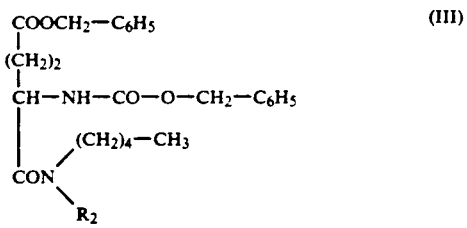

b) debenzylating and decarbobenzoxylating the compound of formula (III) dissolved in an inert solvent, such as methanol, reacting it at ambient temperature and pressure with hydrogen in the presence of a catalytically-effective quantity of a hydrogenation catalyst and recovering from the reaction mass the compound (II),

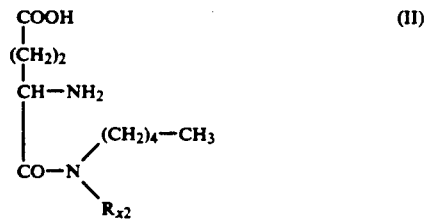

c) reacting the derivative of formula (II) under Schotten-Bauman conditions with an equimolecular quantity of an acyl chloride of the formula $R_1$—CO—Cl in which $R_1$ has the meaning attributed to it above, at a temperature of from 0° to 15° C. and recovering from the reaction mass the (R) 5-pentylamino-5-oxopentanoic derivative of formula (I).

2. A method as in claim 1, wherein the reaction of step a) is carried out in a solvent selected from chloroform, tetrahydrofuran and dioxan, with the reagents in a stoichiometric ratio.

3. A method as in claim 1, wherein, in step b), palladium supported on carbon is used as the catalyst in a ratio of from 0.02 to 0.001 atoms of palladium per mole of compound (III).

* * * * *